United States Patent
Makovec et al.

(12)

(10) Patent No.: US 6,323,216 B1
(45) Date of Patent: Nov. 27, 2001

(54) BASIC DERIVATIVES OF BENZ[E] ISOINDOL-1-ONES AND PYRROLO[3,4-C] QUINOLIN-1-ONES WITH 5-HT$_3$-ANTAGONISTIC ACTIVITY, THEIR PREPARATION AND THEIR THERAPEUTIC USE

(75) Inventors: Francesco Makovec, Monza; Andrea Cappelli, Civitella Marittima; Maurizio Anzini, Pianella; Salvatore Vomero, Monteaperti—Castelnuovo Berardenga; Lucio Claudio Rovati, Monza, all of (IT)

(73) Assignee: Rotta Research Laboratorium S.p.A, Milan (IT)

( * ) Notice: Subject to any disclaimer, the term of this patent is extended or adjusted under 35 U.S.C. 154(b) by 0 days.

(21) Appl. No.: 09/417,098

(22) Filed: Oct. 13, 1999

(30) Foreign Application Priority Data

Oct. 13, 1998 (IT) ................................ TO98A0871

(51) Int. Cl.$^7$ ...................... A61K 31/439; C07D 451/02; C07D 453/02
(52) U.S. Cl. .......................... 514/304; 514/305; 514/411; 546/125; 546/133; 548/450
(58) Field of Search ............................ 546/84, 125, 133; 514/292, 411, 304, 305; 548/450

(56) References Cited

U.S. PATENT DOCUMENTS

| | | | |
|---|---|---|---|
| 5,200,413 | 4/1993 | King et al. | 514/299 |
| 5,260,303 | 11/1993 | Becker et al. | 514/30 |
| 5,280,028 | 1/1994 | Flynn et al. | 514/294 |
| 5,399,562 | 3/1995 | Becker et al. | 514/278 |

FOREIGN PATENT DOCUMENTS

| | | |
|---|---|---|
| 0485962A | 5/1992 | (EP) . |
| 0646583A | 4/1995 | (EP) . |
| 0647639A | 4/1995 | (EP) . |
| WO 91/17161A | 11/1991 | (WO) . |
| WO 92/12149A | 7/1992 | (WO) . |
| WO 95/04742 | 2/1995 | (WO) . |
| WO 95/09168 | 4/1995 | (WO) . |
| WO95/ 32209A | 11/1995 | (WO) . |

OTHER PUBLICATIONS

1. "Untersuchungen und Ringschlusse in der Reihe der Methyl–naphthaline" by F. Mayer et al., Berichte 1922, 55, pp. 1835–1861.

2. "Short Communications" by Nelson et al., Biochem. Pharmacol. 1989, 38, pp. 1693–1695.

3. The B–adrenergic transduction system in kidneys from youn and senescent rats by Vanscheeuwijck et al., Eur. J. Pharmacol., 1990, 188, pp. 129–137.

4. [3H]Ketanserin (R41 468), a Selective 3H–Ligand for Serotonin Receptor Binding Sites, by Leysen et al., Mol. Pharmacol. 1982, 21, pp. 301–314.

5. "[3H]8–Hydroxy–2–(Di–n–Propylamino) Tetralin Bindfing to Pre–and Postsynaptic 5–Hydroxytryptamine Sites in Variours Regionso f the Rat Brain" by Hall et al. , J. Neurochem. 1985, 44 pp. 1685–1696.. "Near–offset multiple suppression" by Eduard Filpo, The Leading Edge, Jan. 1999, pp. 40–44 "Deep–water multiple suppression in the near–offset range" Eduardo Filpoilva et al., WEG, 69$^{th}$ Annual Meeting, Tulsa, OK, USA Oct.

6. "Vagal Sensory Receptors and their Reflex Effects" by Paintal, Physio. Rev. 1973, 53, pp. 159–227.

*Primary Examiner*—Alan L. Rotman
(74) *Attorney, Agent, or Firm*—Sughrue, Mion, Zinn, Macpeak & Seas, PLLC

(57) ABSTRACT

Novel basic derivatives of benz[e]isoindol-1-ones and pyrrolo[3,4-c]quinolin-1-ones which can be represented by the general formula (I) indicated below are described:

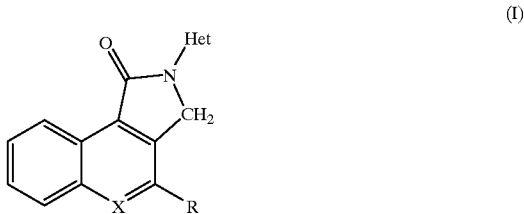

(I)

in which

X is CH or N,

R is H, Cl or OR$_1$ in which R$_1$ is H or an alkyl group having from 1 to 3 carbon atoms, Het is the 3-endotropyl group (that is, the 8-methyl-8-azadicyclo[3.2.1]oct-3-yl group) or the 3-quinuclidyl group (that is, the 1-azadicyclo[2.2.2]oct-3-yl group); these compounds have been found to be potent and selective antagonists of the 5-HT$_3$ serotonin-like receptor and can therefore be used, for example, as antiemetics as well as in various pathological conditions of the central nervous system, and as antitussives.

14 Claims, No Drawings

BASIC DERIVATIVES OF BENZ[E]ISOINDOL-1-ONES AND PYRROLO[3,4-C]QUINOLIN-1-ONES WITH 5-HT$_3$-ANTAGONISTIC ACTIVITY, THEIR PREPARATION AND THEIR THERAPEUTIC USE

The subject of the present invention novel basic derivatives of benz[e]isoindol-1-ones and pyrrolo[3,4-c]quinolin-1-ones which can be represented by the general formula (I) indicated below:

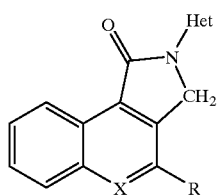

(I)

and in which
X is CH or N,
r is H, Cl or OR$_1$ in which R$_1$ is H or an alkyl group having from 1 to 3 carbon atoms,
Het is the 3-endotropyl group (that is, the 8-methyl-8-azadicyclo[3.2.1]oct-3-yl group) or the 3-quinuclidyl group (that is, the 1-azadicyclo[2.2.2]oct-3-yl group).

The compounds of the present invention have been found to be potent and selective antagonists of the 5-HT$_3$ serotoninergic receptor and can therefore advantageously be used in the treatment of various diseases in man, for example, as anti-emetics, particularly for vomiting associated with antitumoral chemotherapy, and in various pathological conditions of the central nervous system such as, for example, anxiety, depression, schizophrenia, psychosis, Alzheimer's disease and senile dementia, and also as antitussives. Since serotonin is also known to be involved in the regulation of the peristalsis of the gastrointestinal tract, the compounds of the invention can also advantageously be used as prokinetic agents in various pathological conditions connected with hypomotility of the gastrointestinal tract such as, for example, non-ulcerous dyspepsia, reflux oesophagitis and in irritable bowel syndrome.

In addition to the compounds currently used in treatment as anti-emetics, such as Granisetron and Ondasetron, many publications and patents describe novel compounds with 5-HT$^3$ antagonistic activity. Thus, for example, U.S. Pat. No. 5,200,413 describes N-azadicyclo-indol-1-carboxyamides with 5-HT-antagonistic activity; U.S. Pat. No. 5,260,303 describes azacyclo-imidazopyridines with 5-HT$_3$-antagonistic activity, U.S. Pat. No. 5,280,028 describes benzimidazole derivatives active as 5-HT$_3$-antagonists and 5-HT$_4$-antagonists, U.S. Pat. No. 5,399,562 describes indolone derivatives substituted with groups such as endotropyl and quinuclidyl groups. Recently, tropyl-azaindole derivatives with mixed 5-HT$_3$- and sigma-oppioid-antagonist activity having antitussive activity (WO 04742-A-1995), 1-heteroaryl-4-alkyl-4-aminopiperidine derivatives which easily overcome the blood-brain barrier [EP-647639-A (1995)], tetrahydrobenzimidazole derivatives with mixed anti-5-HT$_3$ and H$_3$ histamine activity [WO 9509168-A(1995)] and imidazol-4-yl-piperidine derivatives with mixed anti-5-HT$_3$ and -5-HT$_4$ activity (EP-646583-A (1995)] have also been described. All of this research shows that there is a great therapeutic need to find novel, ever more potent, selective and better tolerated drugs with 5-HT$_3$-antagonistic activity. In accordance with this need, the object of the present invention is to provide novel drug treatments having potent and selective 5-HT$_3$-antagonistic activity for the treatment of all pathological conditions, both central and peripheral, which are due to poor operation of the 5-HT$_3$ serotoninergic receptor system. Pharmaceutical forms of the compounds of the invention can be prepared by conventional techniques, for example, as tablets, capsules, suspensions, solutions, suppositories or patches, and may be administered orally, parenterally, rectally or transdermally, or as other forms suitable for achieving the therapeutic effect such as, for example, solid preparations for oral use with protracted action which permit controlled release of the active substance over time.

The active ingredient is normally administered to the patient with a reference dose variable from 0.001 to 1 mg/kg of body weight per dose. For parenteral administration, the use of a water-soluble salt of the compounds of the invention, such as the hydrochloride or another non-toxic and pharmaceutically acceptable salt, is preferable. As inactive ingredients, substances commonly used in pharmaceutical technology such as excipients, binders, flavourings, disaggregants, colourings, humectants, etc. may be used.

The method of preparing the derivatives of the invention consists of a series of reactions which comprise:
a) reacting esters of formula (IV)

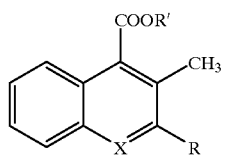

(IV)

prepared as described by Mayer et al (Berichte 1922, 55, 1835–1861), in which X and R have the meanings given above and R' may be methyl or ethyl, with N-bromosuccinimide in the presence of benzoyl peroxide, in an organic solvent such as, for example, carbon tetrachloride, at a temperature between ambient temperature and the reflux temperature of the solvent, for a period of between 1 and 8 h, to give the corresponding 2-bromomethyl derivatives of formula III (see Synthesis scheme 1, step 1);
b) reacting the bromo derivatives of formula III

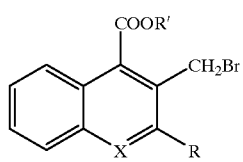

(III)

with a stoichiometric quantity of a heterocyclic amine of formula (II)

NH$_2$-Het  (II)

in which Het is the 3-endotropyl group, that is, the 8-methyl-8-azadicyclo[3.2.1]oct-3-yl group, in the presence of an inert tertiary base which functions as a proton acceptor, or with an excess of the amine (II), at the reflux temperature of an anhydrous solvent, preferably toluene, for a period of between 1 and 24 h, to give the corresponding amide derivatives of formula (I) in accordance with Synthesis scheme 1, step 2. The compounds of formula (I) in which R is OH are prepared by hot acid hydrolysis of the corresponding ethereal derivatives.

Synthesis Scheme 1

Step 1

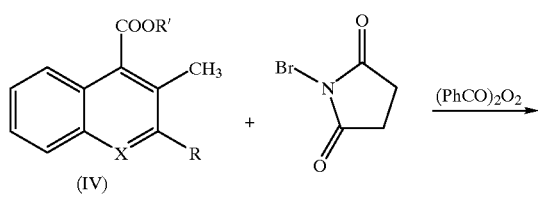

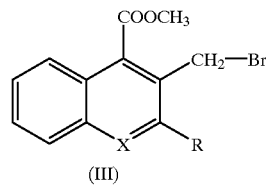

Step 2 in which Het is the 3-endotropyl (8-CH$_3$-8-azadicyclo[3.2.1] oct-3-yl) group (III) + NH$_2$-Het ⟶
(II)

The method for the preparation of the derivatives of the invention in which Het is the 3-quinuclidyl group (that is, the 1-azadicyclo[2.2.2]oct-3-yl group) consists of a series of reactions illustrated by Synthesis scheme 2, comprising: protecting the tertiary endocyclic nitrogen of the 3-aminoquinuclidine by alkylation with allyl bromide, reacting the non-isolated quaternized intermediate (VI) with the appropriate bromine derivative of formula (III) indicated in Scheme 1, to give the quaternary ammoniacal salt of the cyclized compound (V) which, in turn, is not isolated, and deprotecting hot with n-dipropylamine in dimethyl formamide in the presence of a catalytic quantity of Pd(PPh$_3$)$_2$Cl$_2$ to give amide derivatives of formula (I) according to Synthesis scheme 2, step 3, in which Het is the 3-quinuclidyl group and X and R have the meanings given above.

Synthesis scheme 2

Step 1

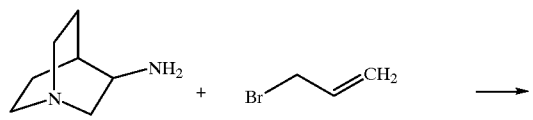

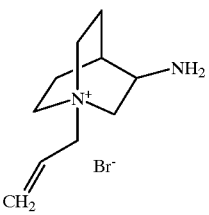

Step 2

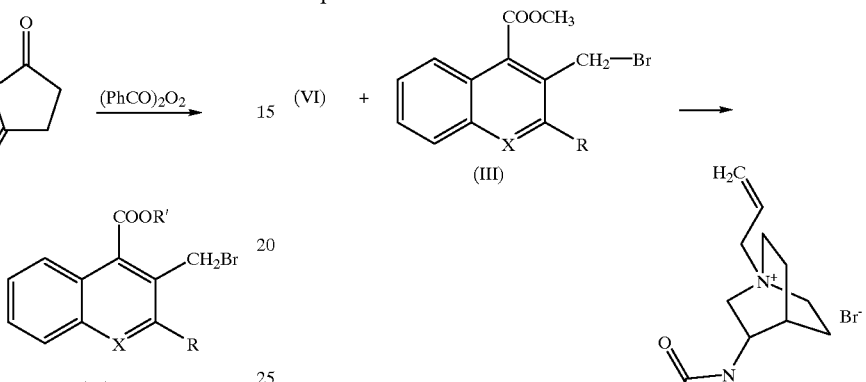

Step 3

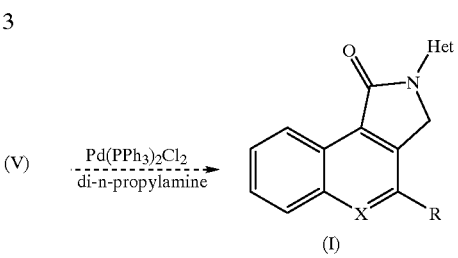

in which Het is the 3-quinuclidyl group (that is, the 1-azadicyclo[2.2.2.]oct-3-yl group).

The following examples are given below to illustrate the invention further.

EXAMPLE 1 endo-2-[8-methyl-8-azadicyclo[3.2.1.]oct-3-yl-2,3-dihydro-1H-benz[e]isoindol-1-one (Compound 1 of Table 1)

A mixture constituted by 10 g (51 mmoles) of 2-methyl-1-naphthalene methyl carboxylate, 9.9 g (55.6 mmoles) of N-bromosuccinimide, and 1.5 g (6.2 mmoles) of benzoyl peroxide in 300 ml of CCl$_4$ was heated under reflux for 2 h. The solvent was evaporated, the residue was taken up with the minimum quantity of CCl$_4$, the succinimide was filtered out, and the filtrate was evaporated under reduced pressure to give 15 g of yellowish oil which was used as such for the subsequent reaction (NMR indicated that this oil was constituted by 85–95% of 2-bromomethyl-1-naphthalene methyl carboxylate). A mixture of 15 g of this oil with 25.9 g (185 mmoles) of endo-3-aminotropane in 500 ml of toluene was heated under reflux for 8 h with azeotropic removal of the methanol evolved in the course of the reaction. The solvent was evaporated under reduced pressure, the residue was taken up with CHCl3, washed with water and then with a saturated NaCl solution, dehydrated and evaporated under reduced pressure. The oily residue, treated with hexane-ethyl acetate, was rendered friable by resting. It was recrystallized from ethyl acetate, to give 8.5 g. Yield 54.5%. Melting point 174–175° C. $^1$H NMR (CDCl$_3$): 1.54–1.61 (m, 4H), 2.15–2.19 (m, 2H), 2.25–2.60 (m, 5H), 3,28 (m, 2H), 4.41 (s, 2H), 4.64 (m, 1H), 7.47–7.67 (m, 3H), 7.90 (d, J=7.6, 1H), 7.97 (d, J=8.3, 1H), 9.24 (d, J=8.4, 1H).

EXAMPLE 2
endo-2-[8-methyl-8-azadicyclo[3.2.1]oct-3-yl]-2,3-dihydro-1H-pyrrolo[3,4-c]quinolin-1-one (Compound 2 of Table 1)

The method described in Example 1 was followed with the use of 3-methyl-4-quinoline ethyl carboxylate instead of the 2-methyl-1-napthalene methyl carboxylate. After reaction with N-bromosuccinimide and in the presence of benzoyl peroxide, the corresponding 3-bromomethyl-4-quinoline ethyl carboxylate, a dense yellow-orange oil, was obtained and was reacted with an excess of endo-3-aminotropane in toluene under reflux for 8 h. Upon completion the oily residue obtained was rendered friable and crystallized from an n-hexane-ethyl acetate mixture. Overall yield 38%. Melting point 153–154° C. $^1$H NMR (CDCl$_3$): 1.50–1.65 (m, 4H), 2.14–2.21 (m, 5H), 2.42–2.59 (m, 2H), 3,28 (m, 2H), 4.46 (s, 2H), 4.61 (m, 1H), 7.61–7.79 (m, 2H), 8.15 (d, J=8.4, 1H), 9.05 (m, 2H), MS: m/z 307 (M$^+$, 22).

EXAMPLE 3
endo-2-[8-methyl-8-azadicyclo[3.2.1.]oct-3-yl]-2,3-dihydro-4-chloro-1H-pyrrolo[3,4-c]quinolin-1-one (Compound 3 of Table 1)

This compound was synthesized by following the method used for the synthesis of Compound 1, with the use of 8.7 g (35 mmoles) of 2-chloro-3-methyl-4-quinoline ethyl carboxylate instead of the 2-methyl-1-naphthalene methyl carboxylate and in accordance with the stoichiometry described above. 7.2 g of Compound 3 was obtained (yield 60%). Recrystallization from n-hexane-ethyl acetate gave a pure product which melted at 169–171° C. $^1$H NMR (CDCl$_3$): 1.47–1.66 (m, 4H), 2.16–2.23 (m, 5H), 2.45–2.60 (m, 2H), 3.29 (m, 2H), 4.41 (s, 2H), 4.67 (m, 1H), 7.64–7.83 (m, 2H), 8.09 (d, J=8.3, 1H), 9.04 (d, J=8.6, 1H), MS: m/z 341 (M$^+$, 16).

EXAMPLE 4
endo-2-[8-methyl-8-azadicyclo[3.2.1]oct-3-yl]-2,3-dihydro-4-propoxy-1H-pyrrolo[3,4-c]quinolin-1-one (Compound 4 of Table 1)

This compound was synthesized by following the method used for the synthesis of Compound 1, with the use of 2.6 g (9.5 mmoles) of 2-propoxy-3-methyl-4-quinoline ethyl carboxylate instead of the 2-methyl-2-naphthalene methyl carboxylate and in accordance with the stoichiometry described above. 1.5 g of Compound 4 was obtained (yield 43%). After crystallization from n-hexane-ethyl acetate, a pure compound in the form of colourless needles which melted at 170–171° C. was obtained. $^1$H NMR (CDCl$_3$): 1.08 (t, J=7.4, 3H), 1.48–1.67 (m, 4H), 1.80–1.98 (m, 2H), 2.19–2.23 (m, 5H), 2.43–2,58 (m, 2H), 3.28 (m, 2H), 4.33 (s, 2H), 4.50–4.73 (m, 3H), 7.48 (t, J=7.4, 1H), 7.65 (t, J=8.1, 1H), 7.90 (d, J=8.3, 1H), 8.93 (d, J=9.0, 1H).

EXAMPLE 5
endo-2-[8-methyl-8-azadicyclo[3.2.1]oct-3-yl]-2,3-dihydro-4-hydroxy-1H-pyrrolo[3,4-c]quinolin-1-one (Compound 5 of Table 1)

8 g (24.9 mmoles) of Compound 3 was dissolved in 1 litre of 1N HCl and heated to 80° C. for 4 h with stirring. The reaction mixture was then cooled to 0° C., brought to pH 9 with 5N NaOH and extracted with chloroform. The organic extracts were dehydrated with anhydrous sodium sulphate, filtered and evaporated at reduced pressure to give 7 g of Compound 5 (yield 88%). Crystallization from ethyl acetate, gave a pure compound which melted at 245–246° C. $^1$H NMR (CDCl$_3$): 1.46–1.61 (m, 4H), 2.16–2.23 (m, 5H), 2.43–2.58 (m, 2H), 3.27 (m, 2H), 4.35 (s, 2H), 4.61 (m, 1H), 7.28–7.36 (m, 2H), 7.55 (m, 1H), 8.84 (d, j=8.2, 1H), 10.63 (br s, 1H), MS: m/z 323 (M$^+$, 28).

EXAMPLE 6
(R,S)-2-[1-azadicyclo[2.2.2]oct-3-yl]-2,3-dihydro-1H-benz[e]isoindol-1-one (Compound 6 of Table 1)

A suspension of 11.2 g (56 mmoles) of 3-aminoquinuclidine dihydrochloride, 22 g (207 mmoles) of anhydrous Na$_2$CO$_3$, and 300 ml of ethanol was heated under reflux in an inert atmosphere with vigorous stirring for 1 h and was then cooled to ambient temperature and supplemented with 4.8 ml (55 mmoles) of allyl bromide. The mixture was allowed to react with stirring at ambient temperature for 20 min. and then heated under reflux for 1 h and finally supplemented with 14.6 g (50 mmoles) of 2-bromomethyl-1-naphthalene methyl carboxylate (prepared as described in the synthesis method of Example 1) dissolved in the minimum quantity of ethanol. The resulting mixture was heated under reflux for 12 h. The solvent was evaporated under reduced pressure and the residue was taken up with 500 ml of dimethyl formamide. The solid which had not dissolved was filtered out and the filtrate was supplemented with 40 ml (292 mmoles) of dipropylamine and 0.5 g (0.71 mmoles) of Pd(PPh$_3$)$_2$Cl$_2$. The resulting mixture was heated to 100° C. for about 30 minutes in an inert nitrogen atmosphere and then poured into water and ice and extracted with CHCl$_3$. The extracts were washed thoroughly with water, dehydrated over sodium sulphate and evaporated at reduced pressure. The semi-solid residue which was obtained was solidified as a result of repeated washings with ethyl ether. 5.1 g of pure, solid, microcrystalline Compound 6 was thus obtained. Yield 34%. Melting point 138–141° C. $^1$H NMR (CDCl$_3$): 1.59–1.96 (m, 4H), 2.20 (m, 1H), 2.89–3.18 (m, 5H), 3.41 (m, 1H), 4.48 (t, J=8.3, 1H), 4.64 (m, 2H), 7.49–7.68 (m, 3H), 7.90 (d, J=8.1, 1H), 7.98 (d, J=8.4, 1H), 9.20 (d, J=8.3, 1H).

EXAMPLE 7
(S)-2-[1-azadicyclo[2.2.2]oct-3-yl]-2,3-dihydro-1H-benz[e]isoindol-1-one (Compound 7 of Table 1)

The (S) enantiomer of Compound 6 was prepared by following the method described above for Compound 6, with the use of (S)-3-aminoquinuclidine dihydrochloride instead of (R,S)-3-aminoquinuclidine dihydrochloride. Yield 32%. Melting point 152–154° C.

EXAMPLE 8
(R)-2-[1-azadicyclo[2.2.2]oct-3-yl]-2,3-dihydro-1H-benz[e]isoindol-1-one (Compound 8 of Table 1)

The (R) enantiomer of Compound 6 was prepared by following the method described above for Compound 6, with the use of (R)-3-aminoquinuclidine dihydrochloride instead of (R,S)-3-aminoquinuclidine dihydrochloride. Yield 35%. Melting point 155–157° C.

EXAMPLE 9
(R,S)-2-[1-azadicyclo[2.2.2]oct-3-yl]-2,3-dihydro-1H-pyrrolo[3,4-c]quinolin-1-one (Compound 9 of Table 1)

The method described for the preparation of Compound 6 was followed, with the use of 3-bromomethyl-4-quinoline ethyl carboxylate instead of 2-bromomethyl-1-naphthalene methyl carboxylate. Upon completion, the oily residue obtained was rendered friable with n-hexane to give an amorphous solid without a definite melting point. Calculated analysis for $C_{18}H_{19}N_3O$: C, 73.69; H, 6.53; N, 14.32. Found: C, 73.98, H, 6.66, N, 13.99.

Some derivatives of formula (I) produced in accordance with the invention are given in Table 1 below with some identifying chemical and physical characteristics, without thereby in any way limiting the spirit and subject of the invention.

d) Affinity For the 5-$HT^{1A}$ Receptors

The method of Hall et al (J. Neurochem. 1985, 44, 1685–1696) was followed with slight modifications. Rat hippocampus was used to produce a pellet having a final concentration of 4 mg of tissue/sample. Specific activity of the tracer: 137 Ci/mmole; incubation time 10 min; incubation temperature: 37° C. Specific binding: 80% of the total; Kd=$2.3 \times 10^{-9}$M.

TABLE 1

Compounds of formula (I)

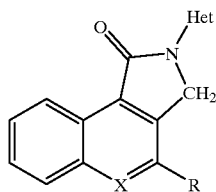

| Compounds | X | Het | R | Formula | Melting point | Crystallization solvents |
|---|---|---|---|---|---|---|
| 1 | CH | 3-endo-tropyl[(1)] | H | $C_{20}H_{22}N_2O$ | 174–175° C. | ethyl acetate |
| 2 | N | 3-endo-tropyl | H | $C_{19}H_{21}N_3O$ | 153–154° C. | n-hexane-ethyl acetate |
| 3 | N | 3-endo-tropyl | Cl | $C_{19}H_{20}ClN_3O$ | 169–171° C. | n-hexane-ethyl acetate |
| 4 | N | 3-endo-tropyl | $OC_3H_7$ | $C_{22}H_{27}N_3O_2$ | 170–171° C. | n-hexane-ethyl acetate |
| 5 | N | 3-endo-tropyl | OH | $C_{19}H_{21}N_3O_2$ | 245–246° C. | ethyl acetate |
| 6(R,S) | CH | 3-quinuclidyl[(2)] | H | $C_{19}H_{20}N_2O$ | 153–154° C. | n-hexane-ethyl ether |
| 7(S) | CH | 3-quinuclidyl | H | $C_{19}H_{20}N_2O$ | 152–154° C. | n-hexane-ethyl ether |
| 8(R) | CH | 3-quinuclidyl | H | $C_{19}H_{20}N_2O$ | 155–157° C. | n-hexane-ethyl ether |
| 9 | N | 3-quinuclidyl | H | $C_{18}H_{19}N_3O$ | amorphous | — |

[(1)]3-tropyl = 8-methyl-8-azadicyclo[3.2.1.]oct-3-yl
[(2)]3-quinuclidyl = 1-azadicyclo[2.2.2]oct-3-yl

DESCRIPTION OF PHARMACOLOGICAL ACTIVITY

In order to evaluate the affinity of the compounds of the invention for the various subtypes of serotoninergic receptors, [3H]-BRL43694 (Granisetron) was used as a marked ligand for the investigation of the 5-$HT_3$ receptors, [3H]-paroxetine was used for the investigation of the serotonin uptake site, [3H]-ketanserine was used for the investigation of the 5-$HT_2$ receptors and [3H]-8-OH DPAT was used for the investigation of the 5HT-1A receptors.

a) Affinity For the 5-$HT_3$ Receptors

The method of Nelson et al. (Biochem. Pharmacol. 1989, 38, 1693–95) was followed with slight modifications. Rat cortex and hippocampus were used to produce a pellet having a final concentration of 20 mg of tissue/sample. Specific activity of the tracer: 81 Ci/mmole; incubation time: 30 min; incubation temperature: 25° C. Specific binding: 70% of the total; Kd=$0.6 \times 10^{-9}$M.

b) Affinity For the Serotonin Uptake Site

The method of Plenge et al (Eur. J. Pharmacol., 1990, 189, 129–134) was followed with slight modifications. The entire rat brain was used to produce a pellet having a final concentration of 2 mg of tissue/sample. Specific activity of the tracer: 29.7 Ci/mmole; incubation time: 60 min.; incubation temperature: 25° C. Specific binding: 75% of the total; Kd=$0.09 \times 10^{-9}$M.

c) Affinity For the 5-$HT_2$ Receptors

The method of Leysen et al (Mol. Pharmacol. 1982, 21, 301–314) was followed with slight modifications. Rat prefrontal cortex was used to produce a pellet having a final concentration of 8 mg of tisssue/sample. Specific activity of the tracer: 80.9 Ci/mmole; incubation time: 20 min; incubation temperature: 37° C. Specific binding: 90% of the total; Kd=$0.5 \times 10^{-9}$M.

It can be seen from the data given in Table 2 that many of the compounds of the invention are potent antagonists of the 5-$HT_3$ subtype receptor. For example Compound 7 has a sub-nanomolar affinity for the 5-$HT_3$ receptor and was the most active of all of the compounds tested. The compounds of the invention were also shown to possess a high selectivity for this receptor since they were very slightly active or inactive at the other receptor subtypes tested. It is also interesting to note that even small structural variations of the compounds of the invention cause a significant loss of affinity for the 5$HT_3$ receptor. Thus, for example, Compound 10, that is, the analogous 3-hexotropyl derivative of the corresponding 3-endotropyl (Compound 1), described herein purely for comparative purposes, was almost 2 orders of logarithmic magnitude less active than Compound 1; similarly, Compound 11 which is also given for comparative purposes, that is endo-2-[8-methyl-8-azadicyclo[3.2.1]oct-3-yl]-2,3-dihydro-1H-pyrrolo[3,4-b]quinolin-1-one, which has a "linear" polycyclic fusion and which is the pyrroloquinoline analogue of Compound 2 was approximately 60 times less active than the latter, in which the polycyclic fusion takes place on the "e" face and is hence angular.

Activity in vivo

The potent 5-$HT_3$-antagonistic activity performed by the compounds of the invention in vitro was confirmed in vivo in the rat in the bradycardial reflex test according to Bezold-Jarisch (Paintal, Physio. Rev. 1973, 53, 159). Serotonin injected i.v. induced a bradycardial effect in the rat. Products 1–9 of the invention, injected in doses of 0.1 mg/kg i.v. 5 minutes before the administration i.v. of 0.03 mg/kg of serotonin completely blocked the bradycardial effect induced thereby. It should be noted that the same compounds injected alone, even in doses 10 times higher, did not induce any variation in cardiac frequency in the rat, thus behaving as pure antagonists.

TABLE 2

Affinity of some compounds of the invention for binding to various serotonin receptor subtypes (Ki (nM) ± SE)

| Compound | 5-HT$_3$ Subtype ([3H]-BRL43694) | 5-HT Uptake ([3H]-paroxetin) | 5-HT$_{2A}$ Subtype ([3H]-ketanserine) | 5-HT$_{1A}$ Subtype ([3H]-8OH-DPAT) |
|---|---|---|---|---|
| 1 | 1.0 ± 0.2 | 632 ± 51 | 21110 ± 2300 | 30619 ± 6460 |
| 2 | 1.3 ± 0.2 | 503 ± 86 | IN (10$^{-6}$M) | IN (10$^{-6}$M) |
| 3 | 2.6 ± 0.4 | 175 ± 30 | IN (10$^{-6}$M) | IN (10$^{-6}$M) |
| 4 | 0.7 ± 0.2 | 108 ± 15 | IN (10$^{-6}$M) | IN (10$^{-6}$M) |
| 5 | 0.9 ± 0.06 | 485 ± 37 | IN (10$^{-6}$M) | IN (10$^{-6}$M) |
| 6 | 0.7 ± 0.08 | 95.8 ± 9.6 | 26477 ± 8700 | IN (10$^{-6}$M) |
| 7 | 0.3 ± 0.09 | — | — | — |
| 8 | 1.8 ± 0.5 | — | — | — |
| 9 | 1.6 ± 0.6 | 123.7 ± 22 | IN (10$^{-6}$M) | IN (10$^{-6}$M) |
| 10* | 85.5 ± 16 | — | — | — |
| 11** | 87 ± 37 | — | — | — |
| serotonin | 118 ± 34 | 738 ± 117 | — | 7.3  1.3 |
| quipazine | 1.8 ± 0.3 | 31.3 ± 2.9 | 1808 ± 476 | 3649 ± 799 |
| Granisetron | 0.6 ± 0.06 | — | — | — |
| 6-NO$_2$-quipazine | — | 0.12 ± 0.01 | — | — |
| 8-OH-DPAT | — | — | — | 1.18 ± 0.13 |

*: 3-hexotropyl analogue of Compound 1
**: compound given for comparative purposes (see test)

What is claimed is:

1. A compound which can be represented by the formula (I) indicated below:

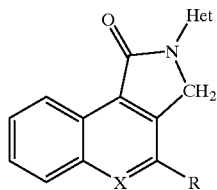

(I)

and in which:

X is CH;

R is H, Cl or OR$_1$ in which R$_1$ is H or an alkyl group having from 1 to 3 carbon atoms;

Het is the 3-endotropyl group (that is, the 8-methyl-8-azadicyclo[3.2.1]oct-3-yl group) or the 3-quinuclidyl group (that is, the 1-azadicyclo[2.2.2]oct-3-yl group), and salts thereof produced from pharmaceutically acceptable inorganic or organic acids.

2. A compound according to claim 1 in which Het is the 3-endotropyl group.

3. A compound according to claim 1 in which Het is the 3-quinuclidyl group.

4. A pharmaceutical composition comprising, as an active substance, a compound according to claim 1 or a pharmaceutically acceptable salt thereof, wherein the compound or salt is present in a pharmaceutically effective amount.

5. A pharmaceutical composition according to claim 4 for therapeutic use in accordance with its activity in the treatment of spontaneous or post-operative nausea and vomiting or nausea or vomiting induced by cytostatic therapy.

6. A pharmaceutical composition comprising, as an active substance, a compound according to claim 1 or a pharmaceutically acceptable salt thereof, wherein the compound or salt is present in a pharmaceutically effective amount, for the treatment of a pathological condition of the CNS connected with an imbalance in the physiological neurone level of serotonin, or with another cause correlated with the mechanism of action of the compound according to claim 1.

7. A pharmaceutical composition according to claim 6, wherein the pathological condition of the CNS connected with an imbalance in the physiological neurone level of serotonin is selected from the group consisting of anxiety, panic attack, psychosis, depression, and Alzheimer's disease.

8. A pharmaceutical composition according to claim 4 for use in the treatment of a disorder of the gastrointestinal system.

9. A pharmaceutical composition according to claim 8, wherein the disorder of the gastrointestinal system is selected from the group consisting of non-ulcerous dyspepsia, oesophagitis due to reflux, irritable colon and motility disturbance.

10. A pharmaceutical composition according to claim 4 for the symptomatic treatment of coughs.

11. A pharmaceutical composition according to claim 4, further comprising pharmaceutically acceptable inactive ingredients selected from the group consisting of a vehicle, binder, flavoring, disaggregant, preservative, humectant, and mixtures thereof, or ingredients which facilitate transdermal absorption or which permit controlled release of the active substance over time.

12. A method for the preparation of a compound of formula (I) in which X and R have the meanings given in claim 1, and Het is the 3-endotropyl group, that is, the 8-methyl-8-azadicyclo[3.2.1]oct-3-yl group, comprising the steps of:

a) reacting an ester of formula (IV)

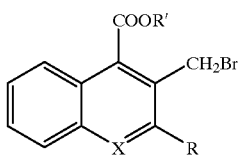

(IV)

in which X and R have the meanings given above and R' may be methyl or ethyl with N-bromosuccinimide in the presence of benzoyl peroxide in an organic solvent at a temperature between ambient temperature and the reflux temperature of the solvent, for a period of between 1 and 8 h, to give the corresponding 2-bromomethyl compound of formula (III);

b) reacting the bromomethyl compound of formula (III)

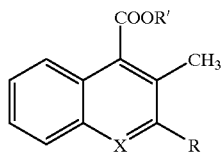

(III)

with a stoichiometric quantity of a heterocyclic amine of formula (II)

NH$_2$-Het    (II)

in which Het is the 3-endotropyl group, in the presence of an inert tertiary base which functions as a proton acceptor, or with an excess of the amine (II), at the reflux temperature of an anhydrous solvent for a period of between 1 and 24 h, to give the corresponding amide compound of formula (I), which is isolated as such or in the form of a pharmaceutically acceptable salt, with the compound of formula (I) in which R is OH being prepared by hot acid hydrolysis of the corresponding ethereal compound.

13. A method according to claim 12, wherein said organic solvent is carbon tetrachloride.

14. A method according to claim 13, wherein said anhydrous solvent is toluene.

* * * * *